United States Patent
Sallak et al.

(10) Patent No.: US 8,225,784 B2
(45) Date of Patent: Jul. 24, 2012

(54) FLUID PRODUCT DISPENSING DEVICE

(75) Inventors: Zakaria Sallak, Lyons (FR); Maxime Kirniak, Sedan (FR)

(73) Assignee: Valois SAS, Le Neubourg (FR)

( * ) Notice: Subject to any disclaimer, the term of this patent is extended or adjusted under 35 U.S.C. 154(b) by 636 days.

(21) Appl. No.: 12/518,232

(22) PCT Filed: Dec. 10, 2007

(86) PCT No.: PCT/FR2007/052464
§ 371 (c)(1),
(2), (4) Date: Jun. 8, 2009

(87) PCT Pub. No.: WO2008/081132
PCT Pub. Date: Jul. 10, 2008

(65) Prior Publication Data
US 2010/0012119 A1  Jan. 21, 2010

(30) Foreign Application Priority Data

Dec. 11, 2006 (FR) ...................................... 06 55411
Jul. 3, 2007 (FR) ...................................... 07 56238

(51) Int. Cl.
*A61M 5/00* (2006.01)
(52) U.S. Cl. .............................. 128/203.21; 128/203.15
(58) Field of Classification Search ............. 128/203.21, 128/203.15, 203.12, 205.21, 203.22, 203.23
See application file for complete search history.

(56) References Cited

U.S. PATENT DOCUMENTS

| | | | | |
|---|---|---|---|---|
| 5,447,151 A | * | 9/1995 | Bruna et al. | 128/203.15 |
| 5,873,360 A | * | 2/1999 | Davies et al. | 128/203.15 |
| 6,240,918 B1 | * | 6/2001 | Ambrosio et al. | 128/203.15 |
| 6,378,519 B1 | * | 4/2002 | Davies et al. | 128/203.21 |
| 7,322,353 B2 | * | 1/2008 | Young et al. | 128/203.15 |
| 7,322,354 B2 | * | 1/2008 | Young et al. | 128/203.15 |
| 7,434,579 B2 | * | 10/2008 | Young et al. | 128/203.15 |
| 7,828,172 B2 | * | 11/2010 | Stradella et al. | 222/36 |
| 2005/0081853 A1 | * | 4/2005 | Young et al. | 128/203.21 |
| 2005/0087188 A1 | * | 4/2005 | Young et al. | 128/203.15 |
| 2008/0142008 A1 | | 6/2008 | Pocock et al. | |

FOREIGN PATENT DOCUMENTS

| | | |
|---|---|---|
| WO | 03/035509 A1 | 5/2003 |
| WO | 2006/079751 A1 | 8/2006 |
| WO | 2007/096111 A2 | 8/2007 |
| WO | 2008/012458 A2 | 1/2008 |

* cited by examiner

*Primary Examiner* — Stephen Crow
(74) *Attorney, Agent, or Firm* — Sughrue Mion, PLLC

(57) ABSTRACT

A fluid dispenser device comprising a body (10), said device further comprising: an elongate flexible strip (20) supporting a plurality of reservoirs (21) each containing a dose of fluid or powder; reservoir-opening means (30) for opening a respective reservoir on each actuation; first displacement means (40) for causing said flexible strip (20) to advance before and/or during and/or after each actuation, so as to bring a full reservoir into register with said reservoir-opening means; and second displacement means (45) for displacing a full reservoir (21) against said opening means (30) each time the device is actuated, the leading end (25) of said flexible strip (20), in the advance direction of said strip, being fastened to a receiver element (50) that is rotatably mounted, said receiver element (50) being fastened to a loaded spring (500) that is adapted to exert a force on said receiver element (50) so as to urge it to turn, such that said receiver (50) exerts a traction force on said elongate strip (20), said traction force being independent of said first and second displacement means (40, 45).

12 Claims, 2 Drawing Sheets

FLUID PRODUCT DISPENSING DEVICE

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said inhaler is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that occurs with inhalers provided with blister strips is connected to the displacement of the strip, and to the storage of the used portion of the strip. Thus, depending on the length of the strip, a large amount of space can turn out to be necessary, and any blockage of the blister strip can prevent the inhaler from operating properly. In addition, when the strip advance device simultaneously pulls on the leading end of the strip so as to avoid it being rolled up poorly, a problem can occur as the number of times the device has been actuated increases, in particular because the diameter of the rolled-up used strip increases progressively.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler provided with a blister strip, in which the storage of the used strip portion is optimized, and the risk of the blister strip blocking is minimized.

The present invention thus provides a fluid dispenser device comprising a body, said device further comprising: an elongate flexible strip supporting a plurality of reservoirs each containing a dose of fluid or powder; reservoir-opening means for opening a respective reservoir on each actuation; first displacement means for causing said flexible strip to advance before and/or during and/or after each actuation, so as to bring a full reservoir into register with said reservoir-opening means; and second displacement means for displacing a full reservoir against said opening means each time the device is actuated, the leading end of said flexible strip, in the advance direction of said strip, being fastened to a receiver element that is rotatably mounted, said receiver element being fastened to a loaded spring that is adapted to exert a force on said receiver element so as to urge it to turn, such that said receiver exerts a traction force on said elongate strip, said traction force being independent of said first and second displacement means.

Advantageously, said traction force is at a maximum when the device is first used and reduces on each actuation as the spring relaxes.

Advantageously, said spring is a spiral spring, a leaf spring, or a helical spring.

Advantageously, said spring is fastened firstly to a fastener pin that cannot turn, and secondly to said rotary receiver element.

Advantageously, said receiver element includes a first fastener member to which there is fastened the strip.

Advantageously, said first fastener member forms a baffle for the strip.

Advantageously, the leading end of the strip forms a loop around said first fastener member.

Advantageously, said receiver element includes a second fastener member to which there is fastened a portion of the spring.

Advantageously, said receiver element is snap-fastened on a support surface, preferably by means of snap-fastener studs, so as to fasten said receiver element both axially and transversally, while enabling it to turn about a fastener pin that cannot turn, and to which there is fastened a portion of the spring.

Advantageously, said receiver element is rotatably fastened on a support surface that is secured to said second displacement means, said support element thus being displaced each time the device is actuated, together with the reservoir to be opened.

Advantageously, said opening means comprise a needle that does not move relative to said body, a reservoir being displaced against said needle each time the device is actuated, said needle penetrating into said reservoir so as to empty it by means of an inhalation flow.

Advantageously, said opening means are controlled by the user inhaling, such that the reservoir is opened and emptied simultaneously by said inhalation flow.

These characteristics and advantages and others of the present invention appear more clearly from the following detailed description, given by way of non-limiting example, and with reference to the accompanying drawings, in which.

Figure 1:
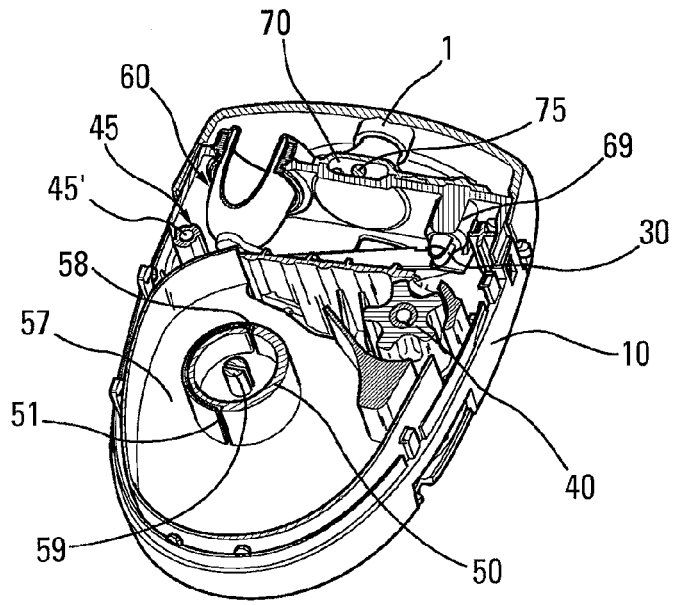
FIG. 1 is a diagrammatic and fragmentary perspective view of a dispenser device constituting an advantageous embodiment of the invention.
Figures 2, 3:
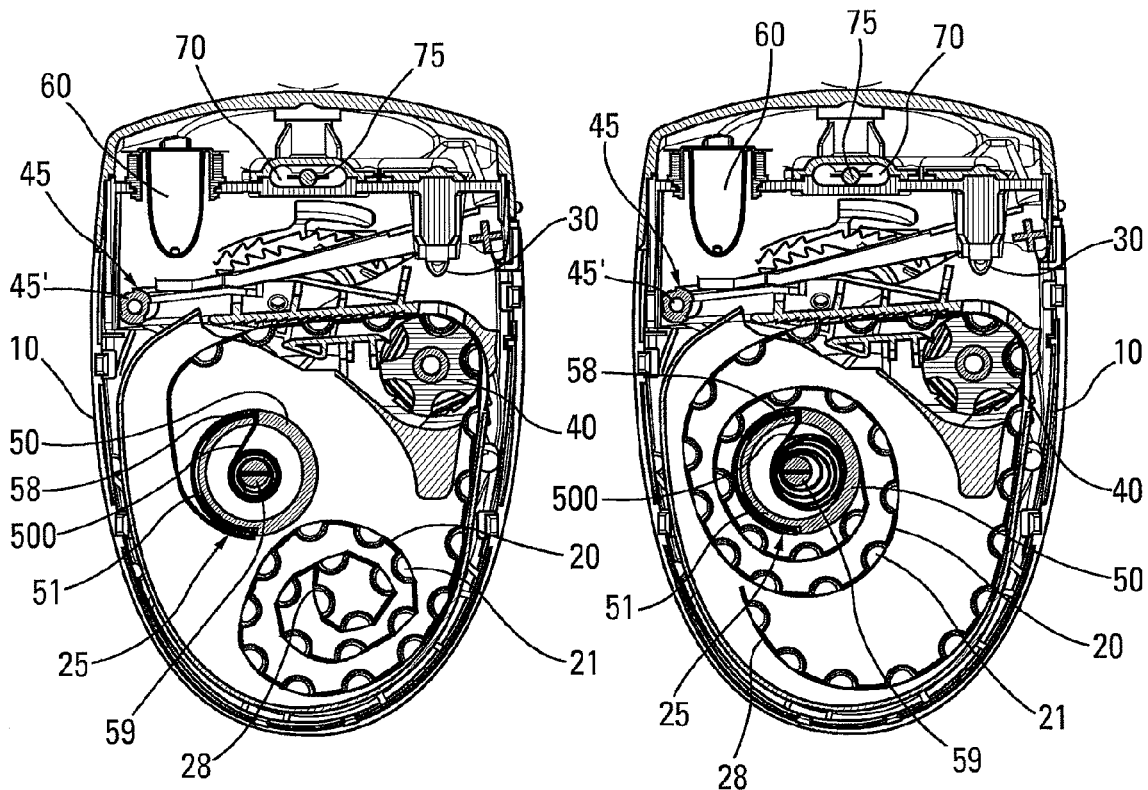
FIG. 2 is a cross-section view of the FIG. 1 device, at the start of use, with a majority of the reservoirs being full.
FIG. 3 is a view similar to the view in FIG. 2, after a plurality of uses, with a majority of the reservoirs being empty.

FIGS. 1 to 3 show an advantageous variant embodiment of a dry-powder inhaler. The inhaler includes a body 10 on which there can be slidably mounted two cover-forming portions (not shown) that are adapted to be opened so as to open and prime the device. The body 10 can be of approximately rounded shape as shown in the figures, but it could have any other appropriate shape. The body 10 includes a mouthpiece or inhaler endpiece 1 that defines a dispenser orifice through which the user inhales while the device is being actuated. The cover can open by pivoting about a common pivot axis, but any other means of opening the device can be envisaged. In a variant, the device could include a single cover instead of two.

Inside the body 10, there is provided a strip 20 of individual reservoirs 21, also called blisters, that is made in the form of an elongate strip 20 on which the blisters 21 are disposed one behind the other in known manner. The blisters 21, preferably containing powder, are not shown in FIG. 1, so as to simplify the drawing for the purpose of clarity. The blister strip 20 is advantageously constituted by a base layer or wall that forms the cavities that receive the doses of powder, and by a closure layer or wall that closes each of said blisters 21 in leaktight manner. Before first use, the blister strip 20 can be rolled-up inside the body 10, preferably in a storage portion, and strip displacement means 40 are provided for progressively unrolling the blister strip and for causing it to advance. Second displacement means 45 are provided for bringing an individual reservoir or respective blister 21 into a dispensing position each time the device is actuated. The strip portion including the empty reservoirs is advantageously adapted to be rolled up in another location of said body 10, preferably a reception portion, as described in greater detail below.

The inhaler includes reservoir-opening means 30 preferably comprising perforator and/or cutter means for perforating and/or cutting the closure layer of the blisters. For example, the reservoir-opening means advantageously comprise a needle 30, that preferably does not move relative to the body 10, and against which a respective blister 21 is displaced on each actuation, by the second displacement means 45. The blister is thus perforated by said needle that penetrates into said blister so as to expel the powder by means of the user inhaling.

The first displacement means 40 are adapted to advance the blister strip 20 before and/or during and/or after each actuation of the device. The second displacement means 45 are adapted to displace the reservoir 21 to be emptied against said perforator and/or cutter means 30 during actuation. The second displacement means 45 can be urged by a resilient element, such as a spring or any other equivalent resilient element, said resilient element possibly being preprimed while the device is being opened. The first displacement means 40 preferably comprise an indexer wheel 40 that receives and guides the blisters. Turning the wheel 40 causes the blister strip 20 to advance. In a particular angular position, a given reservoir 21 is always in a position facing the opening means 30. The second displacement means 45 can comprise a rotary support element that turns about an axis of rotation, said indexer wheel 40 being rotatably mounted on said support element.

An actuation cycle of the device could be as follows. During opening of the device, the two cover-forming lateral portions are moved away from each other by pivoting about the body so as to open the device and thus prime the device. In this position, the indexer wheel 40 cannot be displaced towards the needle 30 since the second displacement means 45 are retained by appropriate blocking means. Preferably, it is while the user is inhaling through the mouthpiece 1 that the blocking means are unblocked, thereby causing said indexer wheel 40 to be displaced towards the needle 30, and thus causing a reservoir 21 to be opened.

In the embodiments shown, the reservoir 21 is displaced towards its open position so as to be opened by the needle 30 that does not move relative to the body 10. However, it can be envisaged that the needle can also be movable during the stage of opening the reservoir 21. For example, the needle could be displaced towards the reservoir 21 while the reservoir 21 is displaced towards the needle. In another variant, it is also possible to envisage that the reservoir 21 and the needle are displaced in the same direction during actuation, the reservoir 21 being displaced quicker in said direction, such that it comes into contact with the needle so as to be opened.

As explained above, it is desirable for the opening means to be actuated by the user inhaling. In order to trigger the reservoir opening means by inhalation, an inhalation trigger system can be provided that advantageously comprises a unit 60 that is displaceable and/or deformable under the effect of inhalation, the unit 60 being adapted to release the blocking means. The unit 60 advantageously comprises a deformable air chamber. The inhalation by the user causes said deformable air chamber 45 to deform, thereby enabling said blocking means to be released, and thus enabling the second displacement means 45 and thus a respective reservoir 21 to be displaced towards its opening position. The reservoir 21 is thus opened only at the moment of inhalation, so that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

The inhaler further includes a dispenser chamber 70 for receiving the dose of powder after a respective reservoir 21 has been opened. The dispenser chamber 70 is advantageously provided with at least one bead 75 that is displaced inside said chamber 70 during inhalation so as to improve dispensing of the air and powder mixture after a reservoir 21 has been opened, in order to increase the effectiveness of the device.

It can be advantageous for the opening means 30, in particular the needle, to be formed directly on said dispenser chamber 70, e.g. at the end of a channel 69 leading to said chamber 70.

After inhalation, when the user closes the device, all of the components return to their initial rest position. The device is thus ready for a new cycle of use.

In an advantageous aspect of the inhaler, the individual reservoirs or blisters 21 are formed on an elongate strip 20 that, initially, is mainly stored in the form of a roll in a storage housing inside the body 10 of the device. Advantageously, the rolled-up blister strip 20 is held by internal walls of said storage housing without its trailing end 28 (in the direction of advance of the blister strip 20) being fastened relative to said body 10, thereby making it easier to assemble the blister-strip roll inside the device. The blister strip 20 is displaced by the user, advantageously by means of the indexer wheel 40 that advantageously presents at least one, and preferably a plurality of recesses 41, having a shape that corresponds to the shape of the blisters. Thus, when the indexer wheel 40 turns, it advances the blister strip 20. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

After opening one or more blisters, the blister-strip portion with the empty reservoirs must be suitable for being stored in easy and compact manner in the device, avoiding any risk of blocking. Advantageously, the used blister strip is rolled-up automatically, once again forming a roll.

In the invention, the leading end 25 of the blister strip 20 is fastened to a receiver element 50 that is rotatably mounted on a support surface 57. The support surface 57 is preferably movable under the effect of the second displacement means 45, i.e. the receiver element 50 is displaced with the reservoir to be emptied, on each actuation. In the embodiment in FIGS. 1 to 3, it is the group comprising the cassette receiving the strip 20, the indexer wheel 40, and the support surface 57 that pivots about the pivot axis 45'. To ensure that the leading portion of the blister strip 20, namely the portion including the empty blisters, is rolled up properly in the reception portion, the rotary receiver element 50 is adapted to exert a traction force on the strip 20, in particular on its leading end 25. Thus, any risk is avoided of the strip being rolled up poorly, e.g. folding up concertina-like, etc. The traction force is exerted by a spring 500 that urges said receiver element 50 to turn, and thus pull on the strip. In particular, the spring can be a spiral spring, a leaf spring, or a helical spring.

Figure 4:
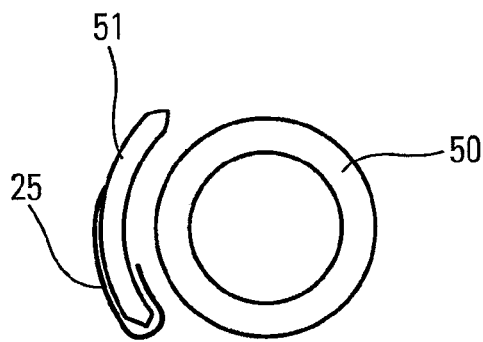
FIGS. 4 to 8 are diagrams showing variant embodiments of the receiver element.
Figure 5:
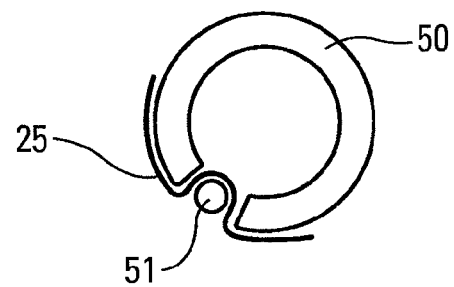
Figure 6:
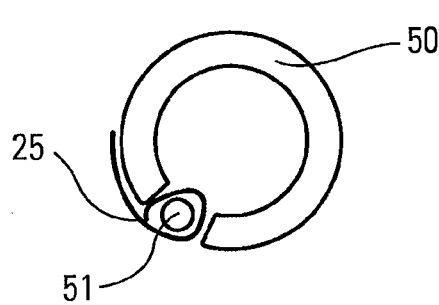
Figure 7:
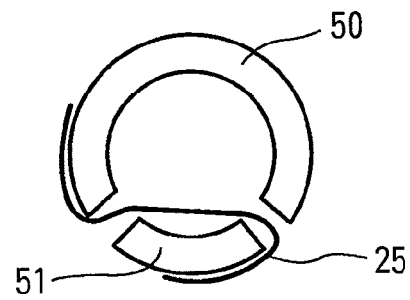
Figure 8:
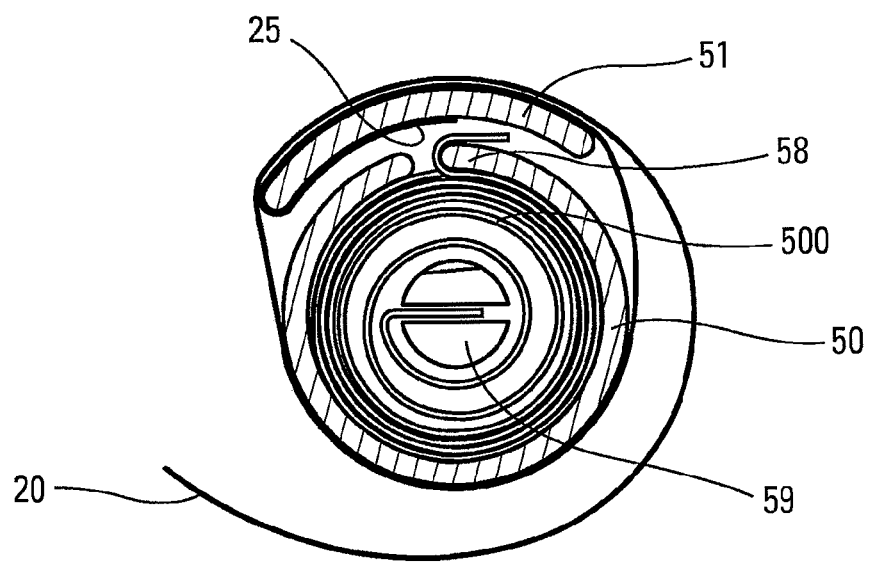

FIGS. 1 to 3 show an advantageous variant embodiment, in which the receiver element 50 forms a cylinder that is rotatably mounted around a fastening pin 59 that does not turn, and to which there is fastened a portion, preferably an end, of the spring 500. Thus, in this embodiment, the spring 500 is disposed around said fastening axis 59, inside said cylinder forming the receiver element 50. Advantageously, the leading end 25 of the blister strip 20 is fastened to a first fastener member 51 that can form a baffle so as to trap the strip 20. Various variants are shown in FIGS. 4 to 8. In FIGS. 4, 7, and 8, the leading end 25 of the strip 20 is curved around an angle member 51 of the receiver element 50, whereas in FIG. 6, it forms a loop around a stud 51. The important point being to provide a fastening that is sufficient to withstand the force of the spring 500 that starts at its maximum and progressively decreases. The other end of the spring 500 can be fastened to a second fastener member 58 of the receiver element 50, said second fastener member also being suitable for forming a baffle for a portion of the spring, preferably its other end, as shown in FIGS. 2, 3, and 8.

The spring 500 is primed before first use or during assembly, and in obvious manner, the maximum traction force exerted on the strip 20 is not enough to tear, deform, or displace the strip 20 in the absence of actuation. On each actuation, the spring relaxes progressively, causing the receiver element 50 to turn. The characteristics of the spring 500 are preferably selected so that it exerts a traction force up to the final doses, but in some applications, it can be sufficient for the traction force to be exerted only at the start of use, so as to guarantee that the portion of strip with the empty reservoirs begins to roll up properly.

The receiver element 50 is preferably fastened on the support surface 57, in particular snap-fastened, so that it can be displaced only in turning, but neither laterally (or transversally), nor vertically (or axially). The snap-fastening can advantageously be achieved by means of snap-fastening lugs, so as to limit friction during turning.

The traction force exerted by the rotary element 50 on the strip 20 is completely independent of the first displacement means, namely the indexer wheel 40 that advances the strip on each actuation. This makes it possible to guarantee that the traction force does not depend on the rolled-up diameter of the roll of used blister strip, as would occur if the turning of the rotary receiver element 50 was correlated to the turning of the indexer wheel 40. It is also completely independent of the second displacement means 45, such that the invention avoids having to provide relatively complex actuator means in order to create a traction force on the strip while the inhaler is being actuated. This simplifies the manufacture and the assembly of the inhaler.

Advantageously, the receiver element 50 is disposed approximately at the center of the reception portion. The reception portion can include guide walls, in particular an external guide wall that is curved, e.g. cylindrical, and against which the blister strip 20 slides. An internal guide wall can also be provided at the inlet to the reception portion, and preferably extends approximately parallel to the external guide wall, so as to form a guide channel for the blister strip 20. The guide walls further facilitate proper rolling up of the blister strip 20 around the receiver element 50.

The present invention therefore makes it possible to provide a dry-powder inhaler that performs the following functions in particular:

a plurality of individual doses of powder are stored in individual sealed reservoirs, e.g. 30 or 60 doses stored on a rolled-up strip;

the powder is released by perforation that is achieved by the user inhaling, the blister being perforated by means of an inhalation detector system that is coupled to a preprimed release system;

appropriately-shaped drive means are engaged with blisters so as to displace the blister strip on each actuation, and bring a new reservoir into a position in which it is to be opened by appropriate opening means; and safe and reliable storage of the used portion of the strip, by being rolled up around a rotary element that is adapted to pull on the strip on each actuation, the traction being completely independent of the first displacement means, namely the indexer wheel 40 that is used to advance the blister strip 20.

Other functions are also provided by the device of the invention as described above. It should be observed that the various functions, even if they are shown as being provided simultaneously on the various embodiments of the inhaler, could be implemented separately. En particular, the inhalation trigger mechanism could be used independently of the type of reservoir-opening means, independently of the use of a dose indicator, independently of the way in which the individual reservoirs are arranged relative to one another, etc. The prepriming means and the inhalation trigger system could be made in some other way. The same applies for other component parts of the device.

Various modifications can also be envisaged by a person skilled in the art, without going beyond the ambit of the present invention, as defined by the accompanying claims.

The invention claimed is:

1. A fluid dispenser device comprising a body, said device further comprising: an elongate flexible strip supporting a plurality of reservoirs each containing a dose of fluid or powder; reservoir-opening means for opening a respective reservoir on each actuation; first displacement means for causing said flexible strip to advance before and/or during and/or after each actuation, so as to bring a full reservoir into register with said reservoir-opening means; and second displacement means for displacing a full reservoir against said opening means each time the device is actuated, said device being characterized in that the leading end of said flexible strip, in the advance direction of said strip, is fastened to a receiver element that is rotatably mounted, said receiver element being fastened to a loaded spring that is adapted to exert a force on said receiver element so as to urge it to turn, such that said receiver exerts a traction force on said elongate strip, said traction force being independent of said first and second displacement means.

2. A device according to claim 1, in which said traction force is at a maximum when the device is first used and reduces on each actuation as the spring relaxes.

3. A device according to claim 1, in which said spring is a spiral spring, a leaf spring, or a helical spring.

4. A device according to claim 1, in which said spring is fastened firstly to a fastener pin that cannot turn, and secondly to said rotary receiver element.

5. A device according to any preceding claim, in which said receiver element includes a first fastener member to which there is fastened the strip.

6. A device according to claim 5, in which said first fastener member forms a baffle for the strip.

7. A device according to claim 5, in which the leading end of the strip forms a loop around said first fastener member.

8. A device according to claim 1, in which said receiver element includes a second fastener member to which there is fastened a portion of the spring.

9. A device according to claim 1, in which said receiver element is snap-fastened on a support surface, preferably by means of snap-fastener studs, so as to fasten said receiver element both axially and transversally, while enabling it to turn about a fastener pin that cannot turn, and to which there is fastened a portion of the spring.

10. A device according to claim 1, in which said receiver element is rotatably fastened on a support surface that is secured to said second displacement means, said support element thus being displaced each time the device is actuated, together with the reservoir to be opened.

11. A device according to claim 1, in which said opening means comprise a needle that does not move relative to said body, a reservoir being displaced against said needle each time the device is actuated, said needle penetrating into said reservoir so as to empty it by means of an inhalation flow.

12. A device according to claim 1, in which said opening means are controlled by the user inhaling, such that the reservoir is opened and emptied simultaneously by said inhalation flow.

* * * * *